(12) United States Patent
Herzig et al.

(10) Patent No.: US 11,053,499 B2
(45) Date of Patent: Jul. 6, 2021

(54) OLIGONUCLEOTIDE SEQUENCES TARGETING TRANSCRIPTION FACTOR TSC22D4 FOR THE TREATMENT OF INSULIN RESISTANCE

(71) Applicant: DEUTSCHES KREBSFORSCHUNGSZENTRUM STIFTUNG DES ÖFFENTLICHEN RECHTS, Heidelberg (DE)

(72) Inventors: Stephan Herzig, Baldham (DE); Mauricio Berriel Diaz, Dossenheim (DE); Tobias Schafmeier, Mannheim (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 0 days.

(21) Appl. No.: 16/862,930

(22) Filed: Apr. 30, 2020

(65) Prior Publication Data

US 2020/0255834 A1 Aug. 13, 2020

Related U.S. Application Data

(63) Continuation of application No. 15/545,104, filed as application No. PCT/EP2016/053050 on Feb. 12, 2016, now Pat. No. 10,676,739.

(30) Foreign Application Priority Data

Mar. 23, 2015 (EP) ..................................... 15160259

(51) Int. Cl.
*C12N 15/113* (2010.01)
*C12Q 1/68* (2018.01)

(52) U.S. Cl.
CPC ........ *C12N 15/113* (2013.01); *C12N 2310/14* (2013.01); *C12N 2310/3181* (2013.01); *C12N 2310/3231* (2013.01)

(58) Field of Classification Search
None
See application file for complete search history.

(56) References Cited

U.S. PATENT DOCUMENTS

2007/0031844 A1 2/2007 Khvorova et al.
2008/0113351 A1 5/2008 Naito et al.

FOREIGN PATENT DOCUMENTS

WO 2014202602 A1 12/2014

OTHER PUBLICATIONS

Lagana, A. et al., "Computational Design of Artificial RNA Molecules for Gene Regulation." RNA Bioinformatics: Methods in Molecular Biology, 2015, 1269: 393-412.

*Primary Examiner* — Sean McGarry
(74) *Attorney, Agent, or Firm* — Saliwanchik, Lloyd & Eisenschenk

(57) ABSTRACT

The present invention relates to oligonucleotide inhibitors of the TSC22D4 activity or expression and their uses for the prevention, treatment, and/or regulation of insulin resistance, metabolic syndrome and/or diabetes and/or for improving insulin sensitivity in a mammal.

16 Claims, 3 Drawing Sheets

Specification includes a Sequence Listing.

OLIGONUCLEOTIDE SEQUENCES TARGETING TRANSCRIPTION FACTOR TSC22D4 FOR THE TREATMENT OF INSULIN RESISTANCE

CROSS REFERENCE TO A RELATED APPLICATION

This application is a Continuation Application of Co-pending application Ser. No. 15/545,104, filed Jul. 20, 2017; which is a National Stage Application of International Application Number PCT/EP2016/053050, filed Feb. 12, 2016; which claims priority to European Patent Application No. 15160259.6, filed Mar. 23, 2015; both of which are incorporated herein by reference in their entirety.

The Sequence Listing for this application is labeled "SeqList-15 May19-ST25.txt", which was created on May 15, 2019, and is 2 KB. The entire content is incorporated herein by reference in its entirety.

FIELD OF THE INVENTION

The present invention relates to oligonucleotide inhibitors of the TSC22D4 activity or expression and their uses for the prevention, treatment, and/or regulation of insulin resistance, metabolic syndrome and/or diabetes and/or for improving insulin sensitivity in a mammal.

BACKGROUND OF THE INVENTION

In humans, a combination of excessive lipid storage and decreased removal leads to overweight and associated co-morbidities, including insulin resistance, cardiovascular complications, and dyslipidemia (Langin D. In and out: adipose tissue lipid turnover in obesity and dyslipidemia. Cell Metab. 2011 Nov. 2; 14(5):569-70), now affecting more than 1.5 billion people worldwide (Finucane M M, et al. National, regional, and global trends in body-mass index since 1980: systematic analysis of health examination surveys and epidemiological studies with 960 country-years and 91 million participants. Lancet. 2011 Feb. 12; 377 (9765):557-67). Indeed, insulin resistance represents the core component of the so-called metabolic syndrome, ultimately leading to the development of metabolic dysfunction, such as glucose intolerance, pancreatic beta cell failure, and eventually type 2 diabetes.

Impaired insulin secretion (beta-cell), increased hepatic glucose production (liver), and decreased peripheral (muscle) glucose utilization constitute the traditional primary defects responsible for the development and progression of type 2 diabetes mellitus. Beta-Cell failure, ultimately leading to decreased insulin secretion, is now known to occur much earlier in the natural history of type 2 diabetes than originally believed. Additionally, a better understanding of the pathophysiology of type 2 diabetes reveals other etiologic mechanisms beyond the classic triad, now referred to as the ominous octet. In addition to the beta-cell, liver, and muscle, other pathogenic mechanisms include adipocyte insulin resistance (increased lipolysis), reduced incretin secretion/sensitivity (gastrointestinal), increased glucagon secretion (alpha-cell), enhanced glucose reabsorption (kidney), and central nervous system insulin resistance resulting from neurotransmitter dysfunction (brain). Currently, the management of type 2 diabetes focuses on glucose control via lowering of blood glucose (fasting and postprandial) and hemoglobin A(1c). However, the goal of therapy should be to delay disease progression and eventual treatment failure. Treatment should target the known pathogenic disturbances of the disease (i.e., reducing the deterioration of beta-cell function and improving insulin sensitivity). In recent years, treatment strategies have focused on the development of novel therapeutic options that affect many of the defects contributing to type 2 diabetes and that provide durable glucose control through a blunting of disease progression. Optimal management of type 2 diabetes should include early initiation of therapy using multiple drugs, with different mechanisms of action, in combination (DeFronzo R A. (Current issues in the treatment of type 2 diabetes. Overview of newer agents: where treatment is going. Am J Med. 2010 March; 123(3 Suppl):S38-48).

Especially the insensitivity of major metabolic organs against insulin action, including the liver, skeletal muscle and adipose tissue, substantially contributes to disease progression and the ultimate need for pharmacologic intervention to prevent diabetic late complications. Thus, efficient and safe insulin sensitization remains an attractive target and aim in anti-diabetic therapy.

Transcriptional co-factor complexes have been identified as important checkpoints in the coordination of metabolic programs in various tissues, including liver and white adipose tissue (WAT) (for a review, see Sommerfeld A, Krones-Herzig A, Herzig S. Transcriptional co-factors and hepatic energy metabolism. Mol Cell Endocrinol. 2011 Jan. 30; 332(1-2): 21-31).

Kester H A, et al. (in: Transforming growth factor-beta-stimulated clone-22 is a member of a family of leucine zipper proteins that can homo- and heterodimerize and has transcriptional repressor activity. J Biol Chem. 1999 Sep. 24; 274(39):27439-47) describe that TGF-beta-stimulated clone-22 (TSC-22) encodes a leucine zipper-containing protein that is highly conserved during evolution.

Furthermore, Jones et al. (in Jones, A., et al., Transforming growth factor-beta1 Stimulated Clone-22 D4 is a molecular output of hepatic wasting metabolism. EMBO Mol Med. 2013 February; 5(2):294-308) describe that as a molecular cachexia output pathway, hepatic levels of the transcription factor transforming growth factor beta 1-stimulated clone (TSC) 22 D4 were increased in cancer cachexia. Mimicking high cachectic levels of TSC22D4 in healthy livers led to the inhibition of hepatic VLDL release and lipogenic genes, and diminished systemic VLDL levels under both normal and high fat dietary conditions. Therefore, hepatic TSC22D4 activity may represent a molecular rationale for peripheral energy deprivation in subjects with metabolic wasting diseases, including cancer cachexia.

Kulozik, Ph., et al. (Hepatic deficiency in transcriptional co-factor TBLI promotes liver steatosis and hypertriglyceridemia. 2011 Cell Metab. 13: 389-400) describe that the impaired hepatic expression of transcriptional cofactor transducin beta-like (TBL) 1 represents a common feature of mono- and multigenic fatty liver mouse models. The liver-specific ablation of TBL1 gene expression in healthy mice promoted hypertriglyceridemia and hepatic steatosis under both normal and high-fat dietary conditions. As TBL1 expression levels were found to also inversely correlate with liver fat content in human patients, the lack of hepatic TBLI/TBLRI cofactor activity may represent a molecular rationale for hepatic steatosis in subjects with obesity and the metabolic syndrome.

Berriel Diaz, M., et al. (Nuclear receptor co-factor RIP140 controls lipid metabolism during wasting in mice. 2008. Hepatology 48: 782-791) describe that by preventing the mobilization of hepatic TG stores, the induction of RIP140 in liver provides a molecular rationale for hepatic steatosis in starvation, sepsis, or cancer cachexia. Inhibition of hepatic RIP140 transcriptional activity might, thereby, provide an attractive adjunct scheme in the treatment of these conditions.

Farese et al. (in: The problem of establishing relationships between hepatic steatosis and hepatic insulin resistance. Cell Metab. 2012 May 2; 15(5):570-3) describe that excessive deposition of fat in the liver (hepatic steatosis) is frequently accompanied by hepatic insulin resistance.

Major classes of anti-diabetic and/or insulin sensitizing drugs include sulfonyl ureas, metformin, thiazolidine diones, alpha-glucosidase inhibitors, incretin mimetics, and dipeptidyl-peptidase 4 inhibitors, all of which are associated with severe limitations (for review see Moller, Metabolic disease drug discovery—"hitting the target" is easier said than done. Cell Metab. 2012 Jan. 4; 15(1):19-24).

Despite the key role of insulin resistance in the pathogenesis of type 2 diabetes, effective and safe insulin sensitizers are still lacking. Indeed, current drugs of the thiazolidinedione family display a moderate efficacy profile and are accompanied by substantial side effects, including weight gain, increased risk of heart failure, possible increased risk of bladder cancer, and an increased risk for myocardial infarction, e.g. leading to the recent market withdrawal of rosiglitazone.

WO 2013/076501 discloses a screening method for identifying agents useful in the treatment and/or prevention of a disease associated with insulin resistance and/or glucose intolerance which comprises the step of investigating the capacity of a test agent to inhibit the Vps34 signaling pathway and/or the RhoIota3Kappa-02beta signaling pathway. Similarly, WO 2005/059564 discloses a method for scanning molecules that modulate the activity of Retinol Binding Protein 4 (RBP4) and their use in treatment of insulin resistance are described. Also described are methods of diagnosing insulin resistance and related conditions by detecting modulation of RBP4 activity.

WO 2012/158123 relates to a method of treating or preventing insulin resistance syndrome in an animal body by administering an inhibitor of protein kinase RNA-like endoplasmic reticulum kinase (PERK) gene, or a functional variant thereof, or an inhibitor of PERK protein or a functional variant thereof or a method of reducing activity of transcription factors of the FOXO family (Foxo 1, 3a, 4 and 6) by administering an inhibitor of protein kinase RNA-like endoplasmic reticulum kinase (PERK) gene, or a functional variant thereof, or an inhibitor of PERK protein or a functional variant thereof.

WO 2014/202602 generally refers to modulators, in particular inhibitors, of TSC22D4 activity or expression and their uses for the prevention, treatment, and/or regulation of insulin resistance, metabolic syndrome and/or diabetes and/or for improving insulin sensitivity in a mammal. WO 2014/202602 further relates to screening methods in order to identify these modulators.

While the experimental knockdown by means of viral delivery of TSC22D4-directed shRNA or miRNA constructs has been proven to efficiently improve the metabolic status of diabetic animals, siRNA constructs suitable for the efficient and specific knockdown of TSC22D4 in various species upon delivery by different technologies had not yet been identified.

BRIEF SUMMARY

In view of the above described flaws in the background art, the objective of the present invention is to provide a new therapeutic strategy to prevent, treat, and/or regulate insulin resistance, metabolic syndrome and/or diabetes and/or to improve insulin sensitivity.

In a first aspect of the present invention, the above objective is solved by providing an inhibitor of the expression and/or biological activity of TSC22D4 selected from an oligonucleotide that is an interfering ribonucleic acid, PNA (protein nucleic acid) or LNA (locked nucleic acid), comprising at least one the following sequences:

```
                                                  (SEQ ID NO: 1)
         5'-GGACGUGUGUGGAUGUUUAdTdT-3';

(SEQ ID NO: 2)
         5'-GGAUGUUUACGAGAGAGAUdTdT-3';

(SEQ ID NO: 3)
         5'-AGUCCCACCUCAUGUUUGCdTdT-3';
``` an antisense sequence thereof, or functional variants thereof.

```
mhD4-siRNA1:  (NM_030935.3_siRNA_1024; ORF)
                                                  (SEQ ID NO: 1)
Sense:        5'- GGACGUGUGUGGAUGUUUAdTdT -3';

(SEQ ID NO: 4)
Antisense:    5'- UAAACAUCCACACACGUCCdTdT -3';

GC:           47% (w/o TT-overhang)

mD4-siRNA2:   (NM_023910.6_siRNA_993; ORF)
                                                  (SEQ ID NO: 2)
Sense:        GGAUGUUUACGAGAGAGAUdTdT -3';

(SEQ ID NO: 5)
Antisense:    AUCUCUCUCGUAAACAUCCdTdT -3';

GC:           42.1% (w/o TT-overhang)

mhD4-siRNA3:
                                                  (SEQ ID NO: 3)
Sense:        5'- AGUCCCACCUCAUGUUUGCdTdT -3';

(SEQ ID NO: 6)
Antisense:    5'- GCAAACAUGAGGUGGGACUdTdT -3';

GC:           52.6% (w/o TT-overhang)
```

Recently, the inventors have shown that transcriptional regulator transforming growth factor beta1 stimulated clone 22 D4 (TSC22D4) controls hepatic and systemic insulin sensitivity. Liver specific loss of TSC22D4 significantly improved glucose tolerance and insulin sensitivity and counteracted hyperinsulinemia in wild-type mice. ChIP-Seq analysis of the TSC22D4 cistrome in combination with high throughput TSC22D4 target transcriptome studies in healthy animals revealed that major nodes of the insulin signaling pathway were directly or indirectly targeted by TSC22D4, most notably lipocalin 13.

Indeed, down-regulation or overexpression of TSC22D4 in primary mouse hepatocytes as well as in wild-type mice led to the up- or down-regulation of the intracellular insulin signaling pathway, as determined by phosphorylation of Akt/PKB kinase at Ser473 and of GSK3beta at Ser9, in response to acute insulin exposure, respectively. Intriguingly, hepatic inactivation of TSC22D4 in diabetic db/db mice improved glucose intolerance and insulin resistance in these animals and normalized blood glucose to almost healthy levels. In congruence with an overall improvement of the metabolic status in diabetic animals, circulating levels of pro-inflammatory cytokines and resistin were significantly lower in mice with liver-specific TSC22D4 deficiency.

While the experimental knockdown by means of viral delivery of TSC22D4-directed shRNA or miRNA constructs has been proven to efficiently improve the metabolic status of diabetic animals, siRNA constructs suitable for the efficient and specific knockdown of TSC22D4 in various species upon delivery by different technologies had not yet been identified.

The inactivation of TSC22D4 in hepatoma cells did not increase cellular growth but rather decreased proliferation, suggesting that the insulin sensitizing function of TSC22D4 does not result in increased cancer susceptibility in affected cells/or organs. In addition, hepatic inactivation of TSC22D4 also did not cause hypoglycemia.

An "inhibitor" is a substance that can reduce the effectiveness of a catalyst in a catalyzed reaction (either a non-biological catalyst or an enzyme). An inhibitor referred to herein can reduce the effectiveness of the activity of an enzyme; also, an inhibitor referred to herein can reduce the effectiveness of the expression of an enzyme. In the context of the present invention, a preferred inhibitor is an oligonucleotide.

The term "oligonucleotide" generally refers to an interfering ribonucleic acid (iRNA), or protein nucleic acid (PNA) or locked nucleic acid (LNA). The term "oligonucleotide" generally refers to a single-stranded nucleotide polymer made of more than 19 nucleotide subunits covalently joined together. Preferably between 19 and 100 nucleotide units are present, most preferably between 19 and 50 nucleotides units are joined together, as also explained further below.

The sugar groups of the nucleotide subunits may be ribose, deoxyribose or modified derivatives thereof such as 2'-0-methyl ribose. The nucleotide subunits of an oligonucleotide may be joined by phosphodiester linkages, phosphorothioate linkages, methyl phosphonate linkages or by other rare or non-naturally-occurring linkages that do not prevent hybridization of the oligonucleotide. Furthermore, an oligonucleotide may have uncommon nucleotides or non-nucleotide moieties.

The term "oligonucleotide" may also refer, in the context of the specification, to a nucleic acid analogue of those known in the art, for example Locked Nucleic Acid (LNA), or a mixture thereof. The term "oligonucleotide" includes oligonucleotides composed of naturally occurring nucleobases, sugars and internucleoside (backbone) linkages as well as oligonucleotides having non-naturally-occurring portions which function similarly or with specific improved functions. A fully or partly modified or substituted oligonucleotide is often preferred over native forms because of several desirable properties of such oligonucleotides such as for instance, the ability to penetrate a cell membrane, good resistance to extra- and intracellular nucleases, high affinity and specificity for the nucleic acid target. Methods of modifying oligonucleotides in this manner are known in the art.

In some oligonucleotides, sometimes called oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a protein nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

A further modification includes Locked Nucleic Acids (LNAs) in which the 2'-hydroxyl group is linked to the 3' or 4' carbon atom of the sugar ring, thereby forming a bicyclic sugar moiety. The linkage is preferably a methylene ($—CH_2—$)$_n$ group bridging the 2' oxygen atom and the 4' carbon atom, wherein n is 1 or 2. The term "LNA" generally refers to a nucleotide containing one bicyclic nucleoside analogue, also referred to as a LNA monomer, or an oligonucleotide containing one or more bicyclic nucleoside analogues.

Preferred is the inhibitor according to the present invention, wherein the interfering ribonucleic acid is a small interfering ribonucleic acid (siRNA) or small hairpin ribonucleic acid (shRNA) or micro ribonucleic acid (miRNA) or combinations thereof.

Further preferred is the inhibitor according to the present invention, wherein the siRNA has a length of between 19 to 30 nucleotides.

In one aspect, the bioactive agent utilizes "RNA interference (RNAi)". RNAi is a process of sequence-specific, post-transcriptional gene silencing initiated by double stranded RNA (dsRNA) or siRNA. RNAi is seen in a number of organisms such as *Drosophila*, nematodes, fungi and plants, and is believed to be involved in anti-viral defense, modulation of transposon activity, and regulation of gene expression. During RNAi, dsRNA or siRNA induces degradation of target mRNA with consequent sequence-specific inhibition of gene expression. As used herein, a "small interfering RNA" (siRNA) is a RNA duplex of nucleotides that is targeted to the gene of TSC22D4. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' and/or 5' overhang portions. In some embodiments, the overhang is a 3' and/or a 5' overhang 0, 1, 2, 3, 4 or 5 nucleotides in length. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

As used herein, the term "siRNA" refers to a ribonucleic acid (RNA) or RNA analog comprising between about 19 to 50 nucleotides (or nucleotide analogs) capable of directing or mediating the RNA interference pathway. These molecules can vary in length and can contain varying degrees of complementarity to their target messenger RNA (mRNA) in the antisense strand. The term "siRNA" includes duplexes of two separate strands, i.e. double stranded RNA, as well as single strands that can form hairpin structures comprising of a duplex region. The siRNA may have a length of between about 19 to 50 nucleotides, or between about 25 to 50 nucleotides, or between about 30 to 50 nucleotides, or between about 35 to 50 nucleotides, or between about 40 to 50 nucleotides. In one embodiment, the siRNA has a length of between 19 to 30 nucleotides.

The application of siRNA to down-regulate the activity of its target mRNA is known in the art. In some embodiments, mRNA degradation occurs when the anti-sense strand, or guide strand, of the siRNA directs the RNA-induced silencing complex (RISC) that contains the RNA endonuclease Ago2 to cleave its target mRNA bearing a complementary sequence. Accordingly, the siRNA may be complementary to any portion of varying lengths on the PERK gene. The siRNA may also be complementary to the sense strand and/or the anti-sense strand of the TSC22D4 gene. Accordingly, siRNA treatment may be used to silence the TSC22D4 gene, thereby depleting the TSC22D4 protein downstream.

The term "shRNA", as used herein, refers to a unimolecular RNA that is capable of performing RNAi and that has a passenger strand, a loop and a guide strand. The passenger and guide strand may be substantially complementary to each other. The term "shRNA" may also include nucleic acids that contain moieties other than ribonucleotide moieties, including, but not limited to, modified nucleotides, modified internucleotide linkages, non-nucleotides, deoxynucleotides, and analogs of the nucleotides.

miRNAs down-regulate their target mRNAs. The term "miRNA" generally refers to a single stranded molecule, but in specific embodiments, may also encompass a region or an additional strand that is partially (between 10% and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complements" of a particular sequence comprising a molecule. For example, precursor miRNA may have a self-complementary region, which is up to 100% complementary. miRNA probes or nucleic acids of the invention can include, can be or can be at least 60%, 65%, 70%, 75%, 80%, 85%, 90%, 95%, 96%, 97%, 98%, 99% or 100% complementary to their target.

Most preferred is the inhibitor according to the present invention, wherein the siRNA consists of a sequence: according to SEQ ID NO: 1 to 3 an antisense sequence thereof.

Also preferred is the inhibitor according to the present invention, wherein the functional variant thereof comprises at least one modified or substituted nucleotide. The term "functional variant" also includes a fragment, a variant based on the degenerative nucleic acid code or a chemical derivative. A functional variant may have conservative changes, wherein a substituted nucleic acid has similar structural or chemical properties to the replaced nucleic acid. A functional variant may also have a deletion and/or insertion of one or more nucleic acids. It is understood that the functional variant at least partially retains its biological activity, e.g. function, of the TSC22D4 gene, or even exhibits improved biological activity.

Examples of modified oligonucleotides include, but are not limited to oligonucleotides with phosphorothioate backbones (see above) and oligonucleosides with heteroatom backbones, and in particular -$CH_2$—NH—O—$CH2$-, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—]. Also usable are oligonucleotides having morpholino backbone structures. Modified oligonucleotides used as interfering ribonucleic acids may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particular examples include, but are not limited to O[($CH_2$)$_n$O]$_m$$CH_3$, O($CH_2$)$_n$O$CH_3$, O($CH_2$)$_n$$NH_2$, O($CH_2$)$CH_3$, O($CH_2$)$_n$O$NH_2$, and O($CH_2$)$_n$ON[($CH_2$)$_n$$CH_3$)]$_2$, where n and m are from 1 to about 10. Other exemplary oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One exemplary modification includes 2'-methoxyethoxy (2'-O—$CH_2$$CH_2$O$CH_3$, also known as 2'-O-(2-methoxyethyl) or 2'-MOE), i.e., an alkoxyalkoxy group.

Another aspect then relates to a recombinant vector, comprising an oligonucleotide according to the present invention. Generally, the oligonucleotide is inserted into an expression vector, such as a plasmid, for expression. If necessary, the oligonucleotide may be linked to the appropriate transcriptional and translational regulatory control nucleotide sequences recognized by the desired host, although such controls are generally available in the expression vector. The vector is then introduced into the host through standard techniques.

Vectors that express siRNAs within mammalian cells typically use an RNA polymerase III promoter to drive expression of a short hairpin RNA that mimics the structure of an siRNA. The insert that encodes this hairpin is designed to have two inverted repeats separated by a short spacer sequence. One inverted repeat is complementary to the mRNA to which the siRNA is targeted. A string of thymidines added to the 3' end serves as a pol III transcription termination site. Once inside the cell, the vector constitutively expresses the hairpin RNA, which induces silencing of the target gene.

Other suitable vectors include viral vectors, such as adenoviral, retroviral and lentiviral viruses or the respective expression systems (see, for example Catanotto, D. et al. (2002) Functional siRNA expression from transfected PCR products. RNA 8, 1454-1460; Barton, G. M. et al. (2002) Retroviral delivery of small interfering RNA into primary cells. Proc Natl Acad Sci USA. 99(23):14943-5. Abbas-Terki, T. et al. (2002) Lentiviral-mediated RNA interference. Hum. Gene Ther. 13, 2197-2201, and Xia, H. et al. (2002) siRNA-mediate gene silencing in vitro and in vivo. Nat. Biotechnol. 20, 1006-1010).

Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell. Host cells that have been transformed by the oligonucleotide of the invention are then cultured for a sufficient time and under appropriate conditions known to those skilled in the art in view of the teachings disclosed herein to permit the expression of the polypeptide, which can then be recovered.

Other examples can be found in the literature, e.g., in Yang J. et al. (Design, preparation and application of nucleic acid delivery carriers." Biotechnol Adv. 2014 July-August; 32(4):804-17).

Each of the classes of nucleic acids as described herein (e.g., the oligonucleotides and/or the vectors) can be introduced into cells by a number of methods. In lipid-mediated transfection, cells take in non-covalent complexes between nucleic acid and a lipid or polymer reagent by endocytosis. Electroporation utilizes a brief electrical pulse to cause disruptions or holes in the cells' plasma membrane through which nucleic acid enters. Both of these methods successfully deliver any of the RNAi nucleic acids expect viral vectors. Viral vector delivery only occurs by infection of cells with the corresponding virus, usually using helper viruses. Infection of the desired cell line with virus introduces the siRNA or shRNA and knocks down gene expression.

Another aspect of the present invention then relates to a recombinant cell, preferably a recombinant hepatocytic cell, comprising an oligonucleotide according to the present invention, or a recombinant vector according to the present invention. A "cell" according to the invention can be a prokaryotic or eukaryotic cell. A "cell" according to the invention is preferably, and without being limited to it, selected from liver cells. Mammalian cells may be preferably selected from a human, rabbit, mouse or rat. Preferably, the cell is a human cell, e.g. a hepatocytic cell. The term "cell" also includes cells of an animal model. Also, a cell can be part of a tissue culture.

The object of the invention is also solved by a method for producing a pharmaceutical composition, comprising the steps of formulating said at least one inhibitor according to the present invention with at least one pharmaceutically acceptable excipient. The carrier and/or excipient of the pharmaceutical composition must be "acceptable" in the sense of being compatible with the other ingredients of the formulation and not deleterious to the recipient thereof.

Another aspect of the present invention then relates to a pharmaceutical composition, comprising at least one of the inhibitor according to the present invention, the recombinant vector according to the present invention, and the recombinant cell according to the present invention, together with a pharmaceutically acceptable carrier. Preferred is a pharmaceutical composition according to the present invention, wherein said pharmaceutical composition is for administration orally, rectally, transmucosally, transdermally, intestinally, parenterally, intramuscularly, intrathecally, direct intraventricularly, intravenously, intraperitoneally, intranasally, intraocularly, or subcutaneously.

Another aspect of the present invention then relates to the inhibitor according to the present invention, the expression vector according to the present invention, the recombinant cell according to the present invention or the pharmaceutical composition according to the present invention for use in the prevention, regulation, and/or treatment of diseases.

Insulin resistance syndrome makes up a broad clinical spectrum and is defined as any abnormalities associated with insulin resistance. Abnormalities such as the resistance to insulin, diabetes, hypertension, dyslipidemia and cardiovascular disease constitute the insulin resistance syndrome.

The insulin resistance syndrome may be diet-induced insulin resistance and/or obesity-induced insulin resistance. Diet-induced insulin resistance means that the resistance to insulin is induced by a diet high in saturated fat and carbohydrates. Obesity-induced insulin resistance means that the resistance to insulin is induced by a genetic predisposition to obesity or obesity which is due to dietary habits.

Another aspect of the present invention thus relates to the inhibitor according to the present invention, the expression vector according to the present invention, the recombinant cell according to the present invention or the pharmaceutical composition according to the present invention for use in the prevention, regulation, and/or treatment of a disease that is selected from insulin resistance, hypertension, dyslipidemia, coronary artery disease, metabolic syndrome and/or diabetes type 1 or 2, and/or for improving insulin sensitivity, such as, for example, insulin sensitivity in the context of a tumorous disease. Preferably, the insulin resistance syndrome is diet-induced insulin resistance and/or obesity-induced insulin resistance.

The object is further solved by a method for treating and/or preventing a disease selected from insulin resistance, metabolic syndrome and/or diabetes in a subject in need thereof, comprising the step of administering an effective amount of an inhibitor according to the present invention or the pharmaceutical composition according to the present invention to said patient in need thereof.

The disclosed methods may be used for treating any one of the following conditions which are caused by insulin resistance syndrome: insulin resistance, hypertension, dyslipidemia, Type 2 diabetes or coronary artery disease.

The term "prevention" in the context of the present invention shall be understood as a medical intervention which aims to avoid the occurrence of a negative event which most likely leads to the worsening of the condition of a patient having a disease, or to the injury or the death of a healthy and/or ill subject. The "patient in need thereof" can be, without being limited to it, any animal or human suffering from a disease related to insulin resistance syndrome, especially insulin resistance, hypertension, dyslipidemia, Type 2 diabetes or coronary artery disease. Preferably, the subject in need thereof is a human.

The object is further solved by a therapeutic kit, comprising the inhibitor according to the present invention, the recombinant vector according to the present invention, the recombinant cell according to the present invention or the pharmaceutical composition according to the present invention, optionally together with suitable buffers and excipients, and instructions for use.

The object is further solved by a therapeutic kit according to the present invention for use in the prevention, regulation, and/or treatment of a disease, wherein said disease is selected from insulin resistance, hypertension, dyslipidemia, coronary artery disease, metabolic syndrome and/or diabetes type 1 or 2, and/or for improving insulin sensitivity, such as, for example, insulin sensitivity in the context of a tumorous disease.

Recently, the inventors have shown that transcriptional regulator transforming growth factor beta 1 stimulated clone 22 D4 (TSC22D4) controls hepatic and systemic insulin sensitivity. Liver specific loss of TSC22D4 significantly improved glucose tolerance and insulin sensitivity and counteracted hyperinsulinemia in wild-type mice. ChIP-Seq analysis of the TSC22D4 cistrome in combination with high throughput TSC22D4 target transcriptome studies in healthy animals revealed that major nodes of the insulin signaling pathway were directly or indirectly targeted by TSC22D4, most notably lipocalin 13. Indeed, down-regulation or overexpression of TSC22D4 in primary mouse hepatocytes as well as in wild-type mice led to the up- or down-regulation of the intracellular insulin signaling pathway, as determined by phosphorylation of Akt/PKB kinase at Ser473 and of GSK3beta at Ser9, in response to acute insulin exposure, respectively.

Intriguingly, hepatic inactivation of TSC22D4 in diabetic db/db mice improved glucose intolerance and insulin resistance in these animals and normalized blood glucose to almost healthy levels. In congruence with an overall improvement of the metabolic status in diabetic animals, circulating levels of pro-inflammatory cytokines and resistin were significantly lower in mice with liver-specific TSC22D4 deficiency.

Inactivation of TSC22D4 in hepatoma cells did not increase cellular growth but rather decreased proliferation, suggesting that the insulin sensitizing function of TSC22D4 does not result in increased cancer susceptibility in affected cells/or-a ans. In addition, hepatic inactivation of TSC22D4 also did not cause hypoglycemia.

While the experimental knockdown by means of viral delivery of TSC22D4-directed shRNA or miRNA constructs has been proven to efficiently improve the metabolic status of diabetic animals, siRNA constructs suitable for the efficient and specific knockdown of TSC22D4 in various species upon delivery by different technologies had not yet been identified. In order to overcome this problem, the inventors have identified, functionally tested and validated various siRNAs directed against the TSC22D4 mRNA sequence in in vitro knockdown studies using murine Hepa1.6 as well as human Huh7 hepatoma cells as disclosed herein.

The following figures, sequences, and examples merely serve to illustrate the invention and should not be construed to restrict the scope of the invention to the particular embodiments of the invention described in the examples. For the purposes of the present invention, all references as cited in the text are hereby incorporated in their entireties.

BRIEF DESCRIPTION OF THE SEQUENCES

Figure 1:
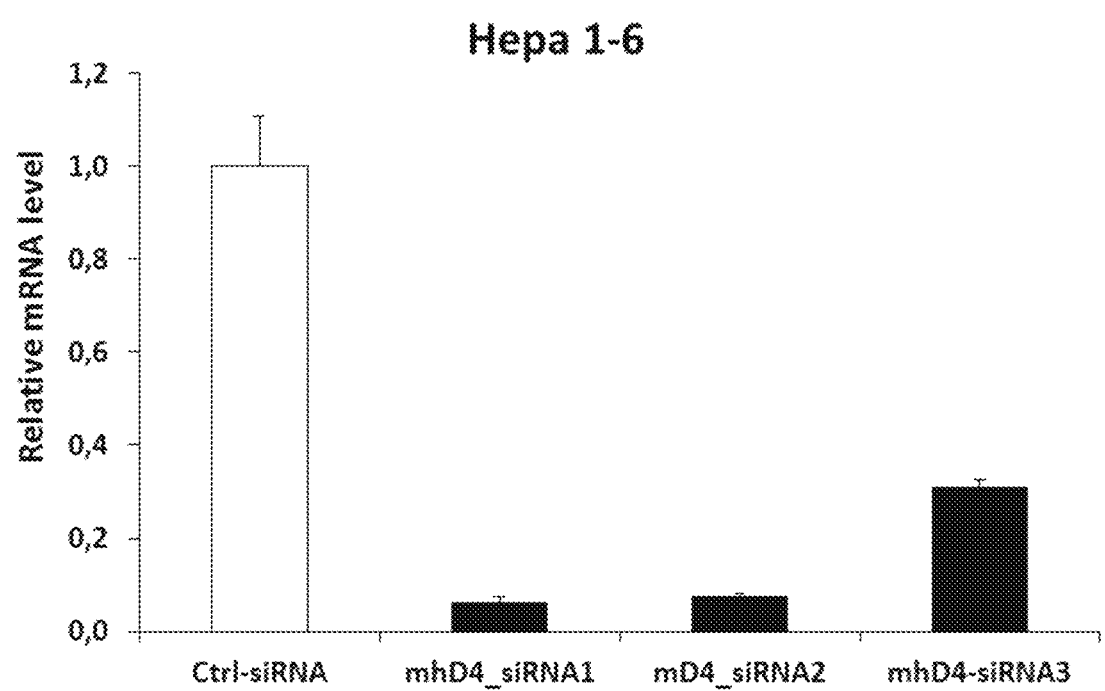
FIG. 1 shows the knockdown efficiency of color-coded, selected TSC22D4-directed siRNAs in murine hepatoma cells. Relative mRNA levels are shown. All other tested siRNA sequences did not show any significant TSC22D4 knockdown in these experiments (not shown).
Figure 2:
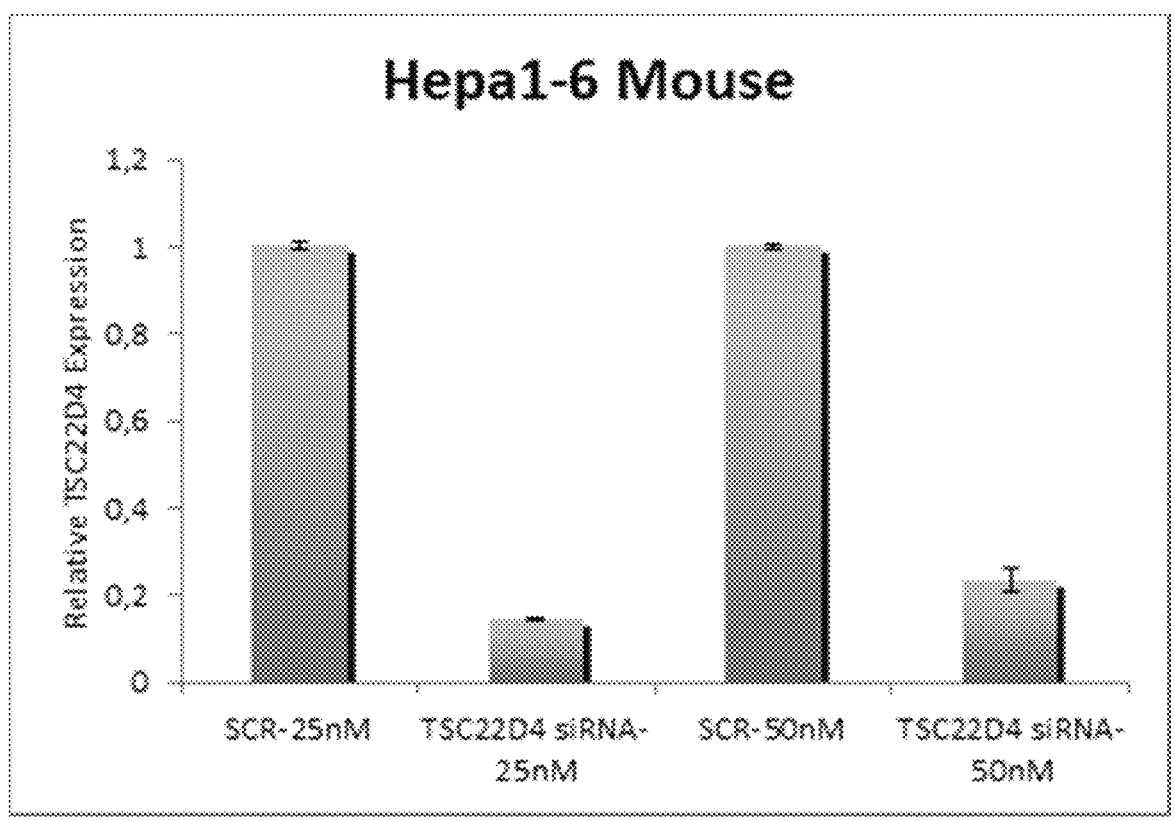
FIG. 2 shows the knockdown efficiency of mhD4-siRNA1 upon transfection into murine Hepa1-6 hepatoma cells towards murine TSC22D4. Relative mRNA levels are shown.
Figure 3:
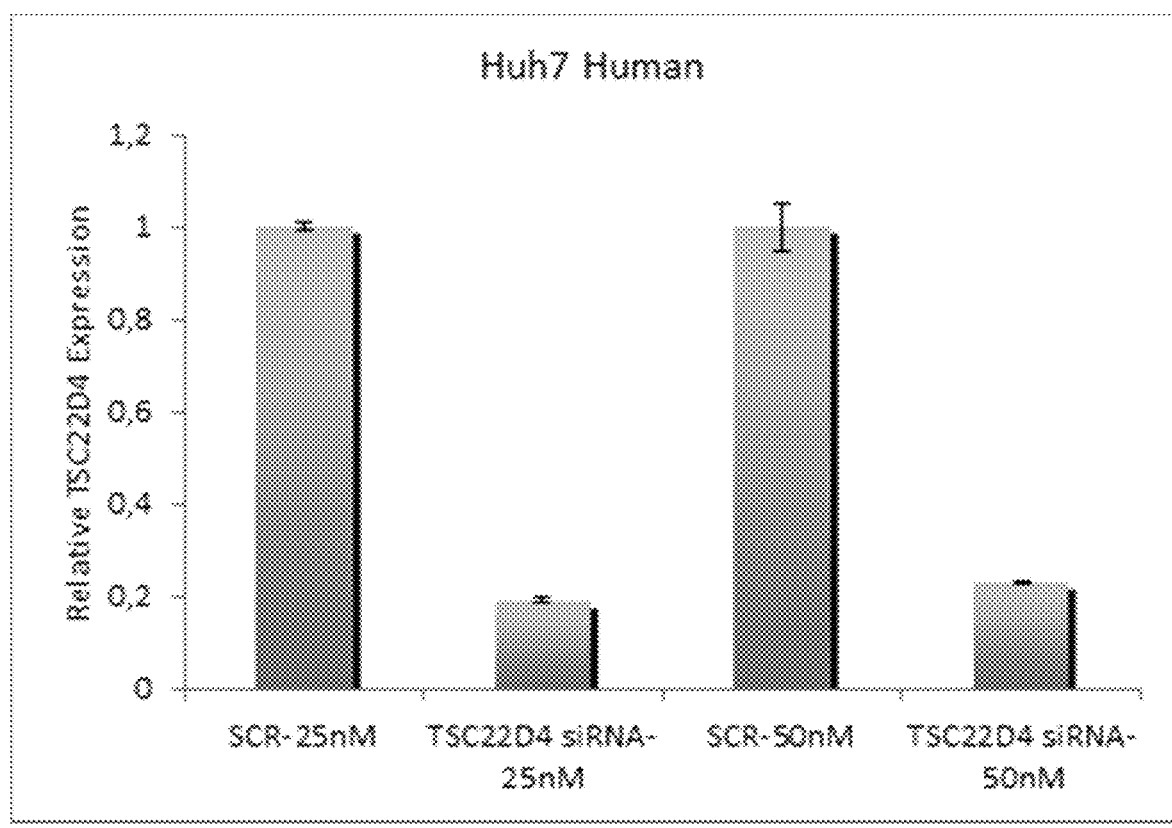
FIG. 3 shows the knockdown efficiency of mhD4-siRNA1 upon transfection into human Huh7 hepatoma cells towards human TSC22D4. Relative mRNA levels are shown.

SEQ ID NOs: 1 to 6 show oligonucleotide sequences according to the present invention.

DETAILED DESCRIPTION

Examples

Recombinant Viruses

Adenoviruses expressing a TSC22D4 or a non-specific shRNA under the control of the U6 promoter, or the TSC22D4 cDNA under the control of the CMV promoter were cloned using the BLOCK-iT Adenoviral RNAi expression system (Invitrogen, Karlsruhe, Germany). Viruses were purified by the cesium chloride method and dialyzed against phosphate-buffered-saline buffer containing 10% glycerol prior to animal injection, as described previously (Herzig S, Hedrick S, Morantte I, Koo S H, Galimi F, Montminy M. CREB controls hepatic lipid metabolism through nuclear hormone receptor PPAR-gamma. Nature. 2003; 426: 190-193. Herzig S, Long F, Jhala U S, Hedrick S, Quinn R, Bauer A, Rudolph D, Yoon C, Puigserver P, Spiegelman B, et al. CREB regulates hepatic gluconeogenesis through the coactivator PGC-1. Nature. 2001; 413: 179-183). AAVs encoding control or TSC22D4-specific miRNAs under the control of a hepatocyte-specific promoter were established as described previously (Rose A J, Frosig C, Kiens B, Wojtaszewski J F, Richter E A. Effect of endurance exercise training on Ca2+ calmodulin-dependent protein kinase II expression and signaling in skeletal muscle of humans. J Physiol. 2007; 583: 785-795).

Animal Experiments

Male 8-12 week old C57Bl/6 and 10 week old db/db mice were obtained from Charles River Laboratories (Brussels, Belgium) and maintained on a 12 h light-dark cycle with regular unrestricted diet. Prior to insulin and glucose tolerance tests, animals were fasted for 4 h. Otherwise, animals were fed ad libitum and had free access to water. For adenovirus injections, $1-2 \times 10^9$ plaque-forming units (pfu) per recombinant virus were administered via tail vein injection. For AAV experiments, $5 \times 10^{11}$ viruses were injected via the tail vein. In each experiment, 6-12 animals received identical treatments and were analyzed under fasted (18 hrs fasting), random fed or fed (18 hrs fasting followed by 6 hrs re-feeding) conditions as indicated. Organs including liver, epididymal and abdominal fat pads, and gastrocnemius muscles were collected after specific time periods, weighed, snap-frozen and used for further analysis. Total body fat content was determined by an Echo MRI body composition analyzer (Echo Medical Systems, Houston, USA). Animal handling and experimentation was done in accordance with NIH guidelines and approved by local authorities.

For the insulin tolerance tests a stock solution of 1 U Insulin/mL was prepared using 0.9% sodium chloride. Mice were fasted for 4 hours prior to the experiment. The body weight of all animals was determined and the blood glucose levels were measured by cutting the tail with a razor blade. The blood drop was put onto a glucometer strip and measured. 1 U insulin/kg body weight was injected to C57Bl/6 and 1.5 U insulin/kg body weight was injected to db/db mice intraperitoneally. The blood glucose levels were monitored after 20, 40, 60, 80 and 120 min.

For the glucose tolerance tests a stock solution of 20% glucose was prepared using 0.9% sodium chloride. Mice were fasted for 4 hours prior to the experiment. The body weight of all animals was determined and the blood glucose levels were measured by cutting the tail with a razor blade. The blood drop was put onto a glucometer strip and measured. 5 µL per gram of 20% glucose solution was injected to C57Bl/6 and db/db mice intraperitoneally. The blood glucose levels were monitored after 20, 40, 60, 80 and 120 min.

Quantitative Taqman RT-PCR

Total RNA was extracted from homogenized mouse liver or cell lysates using Qiazol reagent (Qiagen, Hilden, Germany). cDNA was prepared by reverse transcription using the M-MuLV enzyme and Oligo dT primer (Fermentas, St. Leon-Rot, Germany). cDNAs were amplified using assay-on-demand kits and an ABIPRISM 7700 Sequence detector (Applied Biosystems, Darmstadt, Germany). RNA expression data was normalized to levels of TATA-box binding protein (TBP) RNA.

Human TSC22D4 mRNA expression was measured by quantitative real-time RT-PCR in a fluorescent temperature cycler using the TaqMan assay, and fluorescence was detected on an ABI PRISM 7000 sequence detector (Applied Biosystems, Darmstadt, Germany). Total RNA was isolated using TRIzol (Life technologies, Grand Island, N.Y.), and 1 μg RNA was reverse transcribed with standard reagents (Life Technologies, Grand Island, N.Y.). From each RT-PCR, 2 μl were amplified in a 26 1 PCR reaction using the Brilliant SYBR green QPCR Core reagent kit from stratagene (La Jolla, Calif.) according to the manufacturer's instructions. Samples were incubated in the ABI PRISM 7000 sequence detector for an initial denaturation at 95° C. for 10 min, followed by 40 PCR cycles, each cycle consisting of 95° C. for 15 s, 60° C. for 1 min and 72° C. for 1 min. Human TSC22D4 and Obp2a (LCN13) (determined by Hs00229526_ml and Hs01062934_g1, respectively) (Applied Biosystems, Darmstadt, Germany) mRNA expression was calculated relative to the mRNA expression of hypoxanthine phosphoribosyltransferase 1 (HPRT1), determined by a premixed assay on demand for HPRT1 (Hs01003267_ml) (Applied Biosystems, Darmstadt, Germany). Amplification of specific transcripts was confirmed by melting curve profiles (cooling the sample to 68° C. and heating slowly to 95° C. with measurement of fluorescence) at the end of each PCR. The specificity of the PCR was further verified by subjecting the amplification products to agarose gel electrophoresis.

Protein Analysis

Protein was extracted from frozen organ samples or cultured hepatocytes in cell lysis buffer (Rose A J, Frosig C, Kiens B, Wojtaszewski J F, Richter E A. Effect of endurance exercise training on Ca2+ calmodulin-dependent protein kinase II expression and signaling in skeletal muscle of humans. J Physiol. 2007; 583: 785-795) and 20 μg of protein were loaded onto 4-12% SDS-polyacrylamide gels and blotted onto nitrocellulose membranes. Western blot assays were performed as described (Herzig et al, 2001) using antibodies specific for TSC22D4 (Abcam, Cambridge, UK or Sigma, Munich, Germany), AKT, p-AKT, GSK, p-GSK (Cell signaling, Danvers, USA) or VCP (Abcam).

Plasmids and RNA Interference

For shRNA experiments, oligonucleotides targeting mouse and TSC22D4 (SEQ ID No. 1 to 3), were cloned into the pENTR/U6 shRNA vector (Invitrogen).

Cell Culture and Transient Transfection Assays

Primary mouse hepatocytes were isolated and cultured as described (Klingmuller U, Bauer A, Bohl S, Nickel P J, Breitkopf K, Dooley S, Zellmer S, Kern C, Merfort I, Sparna T, et al. Primary mouse hepatocytes for systems biology approaches: a standardized in vitro system for modelling of signal transduction pathways. IEE Proc Syst Biol. 2006; 153: 433-447). Briefly, male 8-12 week old C57Bl/6 mice were anaesthetized by i.p. injection of 100 mg/kg body weight ketamine hydrochloride and 5 mg/kg body weight xylazine hydrochloride. After opening the abdominal cavity, the liver was perfused at 37° C. with HANKS I (8 g NaCl, 0.4 g KCl, 3.57 g Hepes, 0.06 g $Na_2HPO_4 \times 2\ H_2O$, 0.06 g $KH_2PO_4$ in 1 L distilled $H_2O$, 2.5 mM EGTA, 0.1% glucose, adjusted to pH 7.4) via the portal vein for 5 min and subsequently with HANKS II (8 g NaCl, 0.4 g KCl, 3.57 g Hepes, 0.06 g $Na_2HPO_4 \times 2\ H_2O$, 0.06 g $KH_2PO_4$ in 1 L distilled $H_2O$, 0.1% glucose, 3 mg/ml collagenase CLSII, 5 mM $CaCl_2$, adjusted to pH 7.4) for 5-7 min until disintegration of the liver structure was observed. The liver capsule was removed and the cell suspension was filtered through a 100 μm mesh. The cells were washed and, subsequently, viability of cells was determined by trypan blue staining. 1 000 000 living cells/well were seeded on collagen I-coated six-well plates. After 24 h, cells were infected with recombinant adenoviruses at a multiplicity of infection of 100. For stimulation experiments, primary hepatocytes were treated with PBS (control medium) or insulin at a concentration of 100 nM/6-well for 10 minutes. Cells were harvested 48 h after infection.

Cistrome Analysis of Hepatic TSC22D4

KEGG-Pathway analysis of Chip-Sequencing results were sorted by significance. The Insulin signaling pathway was found to be significantly regulated (p=0.00005). Chip-Sequencing was performed in liver extracts from Flag-TSC22D4 cDNA adenovirus-injected male C57Bl/6 mice 7 days after injection.

Results

The sequences worked very efficiently for both mouse and human TSC as seen in 4 independent experiments (see Figures). There is a nonspecific dTdT overhang attached to each sequence. The sequences matched both the mouse and the human TSC sequence to 100%.

Based on these results, the sequences according to the present invention (SEQ ID No. 1 to 3) were chosen as primary candidates to be used for therapeutic purposes as it shows a superior knockdown efficiency towards TSC22D4 and targets a variety of species, including mouse, non-human primates and humans. The sequences were identified, functionally tested and validated various siRNAs directed against the TSC22D4 mRNA sequence in in vitro knockdown studies using murine Hepa1.6 as well as human Huh7 hepatoma cells. In particular the mhD4-siRNA1 showed a superior knockdown efficiency towards TSC22D4 and targets a variety of species, including mouse, non-human primates and humans.

```
mhD4-siRNA1:  (NM_030935.3_siRNA_1024; ORF)
                                       (SEQ ID NO: 1)
Sense:      5'- GGACGUGUGUGGAUGUUUAdTdT -3';

(SEQ ID NO: 4)
Antisense:  5'- UAAACAUCCACACACGUCCdTdT -3';

GC:         47% (w/o TT-overhang)

mD4-siRNA2:   (NM_023910.6_siRNA_993; ORF)
                                       (SEQ ID NO: 2)
Sense:        GGAUGUUUACGAGAGAGAUdTdT -3';

(SEQ ID NO: 5)
Antisense:    AUCUCUCUCGUAAACAUCCdTdT -3';

GC:           42.1% (w/o TT-overhang)

mhD4-siRNA3:
                                       (SEQ ID NO: 3)
Sense:      5'- AGUCCCACCUCAUGUUUGCdTdT -3';

(SEQ ID NO: 6)
Antisense:  5'- GCAAACAUGAGGUGGGACUdTdT -3';

GC:         52.6% (w/o TT-overhang)
```

The invention claimed is:

1. An inhibitor of expression and/or biological activity of transforming growth factor beta1 stimulated clone 22 D4 (TSC22D4) wherein said inhibitor is an oligonucleotide that is an interfering ribonucleic acid, protein nucleic acid (PNA) or locked nucleic acid (LNA), and wherein said oligonucleotide comprises SEQ ID NO: 1, or the complementary sequence thereof.

2. The inhibitor according to claim 1, wherein the interfering ribonucleic acid is a small interfering ribonucleic acid (siRNA) or small hairpin ribonucleic acid (shRNA) or micro ribonucleic acid (miRNA) or a combination thereof.

3. The inhibitor according to claim 2, wherein the siRNA has a length of 19 to 30 nucleotides.

4. The inhibitor according to claim 2, wherein the siRNA consists of SEQ ID NO: 1.

5. The inhibitor according to claim 1, wherein the functional variants thereof comprise at least one modified or substituted nucleotide.

6. A recombinant vector, comprising an oligonucleotide according to claim 1.

7. A recombinant cell, comprising an oligonucleotide according to claim 1.

8. A pharmaceutical composition, comprising at least one of the inhibitor according to claim 1, together with a pharmaceutically acceptable carrier.

9. The pharmaceutical composition according to claim 8, wherein said pharmaceutical composition is formulated for administration orally, rectally, transmucosally, transdermally, intestinally, parenterally, intramuscularly, intrathecally, direct intraventricularly, intravenously, intraperitoneally, intranasally, intraocularly, or subcutaneously.

10. A method for prevention, regulation, and/or treatment of a disease, and/or for improving insulin sensitivity, wherein said method comprises administering, to a subject in need of such prevention, regulation, treatment, and/or improvement, the inhibitor according to claim 1.

11. The method, according to claim 10, wherein said disease is selected from insulin resistance, hypertension, dyslipidemia, coronary artery disease, metabolic syndrome and diabetes type 1.

12. The method, according to claim 10, wherein the insulin resistance is diet-induced insulin resistance and/or obesity-induced insulin resistance.

13. A therapeutic kit, comprising the inhibitor according to claim 1, optionally together with suitable buffers and excipients, and instructions for use.

14. The therapeutic kit according to claim 13 with instructions for use in the prevention, regulation, and/or treatment of a disease, wherein said disease is selected from insulin resistance, hypertension, dyslipidemia, coronary artery disease, metabolic syndrome and/or diabetes type 1 or 2, and/or for improving insulin sensitivity.

15. The method, according to claim 10, for improving insulin sensitivity in the context of a tumorous disease.

16. The inhibitor according to claim 1, wherein the interfering ribonucleic acid is a siRNA.

* * * * *

SEQUENCE LISTING

<160> NUMBER OF SEQ ID NOS: 6

<210> SEQ ID NO 1
<211> LENGTH: 19
<212> TYPE: RNA
<213> ORGANISM: mus musculus
<220> FEATURE:
<221> NAME/KEY: misc_feature
<222> LOCATION: (19)..(19)
<223> OTHER INFORMATION: dTdT overhang at 3' end

<400> SEQUENCE: 1
ggacgugugu ggauguuua                                        19

<210> SEQ ID NO 2
<211> LENGTH: 19
<212> TYPE: RNA
<213> ORGANISM: mus musculus
<220> FEATURE:
<221> NAME/KEY: misc_feature
<222> LOCATION: (19)..(19)
<223> OTHER INFORMATION: dTdT overhang at 3' end

<400> SEQUENCE: 2
ggauguuuac gagagagau                                        19

<210> SEQ ID NO 3
<211> LENGTH: 19
<212> TYPE: RNA
<213> ORGANISM: homo sapiens
<220> FEATURE:
<221> NAME/KEY: misc_feature
<222> LOCATION: (19)..(19)
<223> OTHER INFORMATION: dTdT overhang at 3' end

<400> SEQUENCE: 3
agucccaccu cauguuugc                                        19

<210> SEQ ID NO 4
<211> LENGTH: 19
<212> TYPE: RNA
<213> ORGANISM: mus musculus
<220> FEATURE:
<221> NAME/KEY: misc_feature
<222> LOCATION: (19)..(19)
<223> OTHER INFORMATION: dTdT overhang at 3' end

<400> SEQUENCE: 4
uaaacaucca cacacgucc                                        19

<210> SEQ ID NO 5
<211> LENGTH: 19
<212> TYPE: RNA
<213> ORGANISM: mus musculus
<220> FEATURE:
<221> NAME/KEY: misc_feature
<222> LOCATION: (19)..(19)
<223> OTHER INFORMATION: dTdT overhang at 3' end

<400> SEQUENCE: 5
aucucucucg uaaacaucc                                        19

<210> SEQ ID NO 6
<211> LENGTH: 19
<212> TYPE: RNA
<213> ORGANISM: homo sapiens
<220> FEATURE:
<221> NAME/KEY: misc_feature

```
<222> LOCATION: (19)..(19)
<223> OTHER INFORMATION: dTdT overhang at 3' end

<400> SEQUENCE: 6
gcaaacauga ggugggacu                                                      19
```